(12) United States Patent
Johansen et al.

(10) Patent No.: US 7,063,970 B1
(45) Date of Patent: Jun. 20, 2006

(54) ENZYMATIC PRESERVATION OF WATER BASED PAINTS

(75) Inventors: Charlotte Johansen, Holte (DK); Claus Crone Fuglsang, Niva (DK)

(73) Assignee: Norozymes A/S, Bagsvaerd (DK)

( * ) Notice: Subject to any disclaimer, the term of this patent is extended or adjusted under 35 U.S.C. 154(b) by 0 days.

(21) Appl. No.: 09/564,935

(22) Filed: May 4, 2000

Related U.S. Application Data

(60) Provisional application No. 60/132,932, filed on May 6, 1999.

(30) Foreign Application Priority Data

May 6, 1999 (DK) ................. 1999 00620

(51) Int. Cl.
    *C12N 9/00* (2006.01)
(52) U.S. Cl. ..................................... 435/183
(58) Field of Classification Search ................ 435/183
    See application file for complete search history.

(56) References Cited

U.S. PATENT DOCUMENTS

| | | | |
|---|---|---|---|
| 5,752,980 A * | 5/1998 | Pedersen et al. | |
| 5,899,212 A * | 5/1999 | Sorensen et al. | |
| 5,912,405 A * | 6/1999 | Schneider et al. | |
| 6,072,015 A * | 6/2000 | Bolle et al. | |
| 6,074,631 A * | 6/2000 | Tsuchiya et al. | |
| 6,080,391 A * | 6/2000 | Tsuchiya et al. | |
| 6,184,014 B1 * | 2/2001 | Echigo et al. | |
| 6,217,942 B1 * | 4/2001 | Bolle et al. | |
| 6,228,128 B1 * | 5/2001 | Johansen et al. | |
| 6,355,461 B1 * | 3/2002 | Henriksen et al. | |
| 2001/0006636 A1 * | 7/2001 | Henriksen et al. | ......... 424/94.4 |
| 2001/0037532 A1 * | 11/2001 | Barfoed et al. | ................ 8/639 |

FOREIGN PATENT DOCUMENTS

| | | |
|---|---|---|
| EP | 0 500 387 A2 | 8/1992 |
| JP | 05247865 * | 9/1993 |
| JP | 06 065526 | 3/1994 |
| JP | 407206644 * | 8/1995 |
| WO | WO 95/27009 | 10/1995 |
| WO | WO 95/27046 | 10/1995 |
| WO | WO 96/10079 * | 4/1996 |
| WO | WO 97/04102 | 2/1997 |
| WO | WO 97/28257 | 8/1997 |
| WO | WO 97/41215 | 11/1997 |
| WO | WO 97/42825 | 11/1997 |
| WO | WO 98/26807 | 6/1998 |
| WO | WO 99/17727 * | 4/1999 |
| WO | 99/23887 | 5/1999 |
| WO | 99/47651 | 9/1999 |
| WO | 00/27204 | 5/2000 |

* cited by examiner

*Primary Examiner*—Michael Meller
(74) *Attorney, Agent, or Firm*—Jason Garbell; Elias J. Lambiris

(57) ABSTRACT

A preserved and/or conserved water based paint composition comprising an oxidoreductase, an oxidizing agent, a binder and at least 10% w/w water.

18 Claims, No Drawings

ENZYMATIC PRESERVATION OF WATER BASED PAINTS

CROSS REFERENCE TO RELATED APPLICATIONS

This application claims priority under 35 U.S.C. 119 of Danish application no. PA 1999 00620 filed on May 6, 1999, and U.S. provisional application no. 60/132,932 filed on May 6, 1999, the contents of which are fully incorporated herein by reference.

FIELD OF THE INVENTION

This invention relates to enzymatically preserved and/or conserved water based paint or fluid compositions used in the production of fossil oil and gas, methods for producing such compositions and the use antimicrobial enzymes in for preservation of water based paints and drilling fluids.

BACKGROUND OF THE INVENTION

Oxidoreductases such as peroxidases and laccases have been suggested as antimicrobial agents in the cleaning industry. The antimicrobial activity of oxidoreductases within fields such as detergents or biofilm removal is described in disclosures such as in WO 97/04102 (NOVO NORDISK), WO 97/42825 (NOVO NORDISK), WO 97/28257 (NOVO NORDISK), WO 97/41215 (NOVO NORDISK) and WO 98/26807 (NOVO NORDISK).

Other prior art is WO 95/27009 (STRICHTING SCHEIKUNDIG ONDERSOZOEK IN NEDERLAND) which suggests that the antimicrobial activities of vanadium chloroperoxidases may be used to prevent fouling of a marine paint surface by immobilising the haloperoxidase in the paint surface and use halides and hydrogen peroxide present in sea water to provide antimicrobial reactions. Examples of this use include vanadium chlorohalopexidase mixed with a solvent based chlorinated rubber antifouling 2000 (AKZO) product or immobilized in a acrylic latex (Sikkens) or a polyacrylamid matrix. The activity of a haloperoxidase in the conventional growth inhibiting agent (the chlorinated rubber antifouling 2000 (AKZO) is however very low due to the solvent of the antifouling agent and poor mixability of the fouling agent with the haloperoxidase.

Also WO 95/27046 (UNILEVER) concerns the use of vanadium haloperoxidase in antimicrobial compositions.

Patent application No. DK98/00477 (unpublished at the date of priority) describes, in particular the section titled "Conservation/preservation of paints" on pages 41–42, the concept and advantage of using oxidoreductases for preservation and/or conservation of water based paints as an alternative to conventional environmentally bio-hazardous biocides, and this invention is a further development of the inventions described in this disclosure.

EP 500 387 A2 discloses haloperoxidases which is used in antiseptic pharmaceutical products.

SUMMARY OF THE INVENTION

As described in Danish patent application No. DK98/00477 (unpublished at the date of priority) conventional water based paints are conventionally preserved by adding non-enzymatic organic biocides such as isothiazoliones to the paint. The trend within paints has been to substitute conventional solvent based paints with water based paints to prevent serious health damage of the users. However water based paints need to be preserved to prevent microbial growth enabled by the increased water activity in the paint, and conventionally huge amounts of conventional biocides are used for this purpose, which has created a desire to find more environment friendly alternatives to the conventional biocides.

We have found that the concept of using oxidoreductases for preservation and/or conservation and/or antifouling of water based paints works in a number of specific paint formulations. Accordingly the invention provides an advantageous alternative for preservation of water based paint by enabling substitution of conventional chemical biocides with enzymatic preservation systems. Thus the invention provides in a first aspect a disinfected and/or preserved and/or conserved water based paint composition comprising an oxidoreductase, an oxidizing agent, at least 10% water and a binder.

We have also found that oxidoreductases advantageously may be used for preservation and/or conservation of fluids used in the oil/gas industry for production of fossil oil/gas and the invention provides in a second aspect a preserved and/or conserved water based fluid composition for use in the recovery of fossil oil and/or gas from drilling sites selected from the group consisting of drilling fluids, completion fluids, fracturing fluids, injection fluids, blocking gels and workover fluids said fluids comprising an oxidoreductase, an oxidizing agent and a biopolymer.

DETAILED DESCRIPTION OF THE INVENTION

Definitions

In the contet of the invention the term "enhancer" is to be construed as a chemical compound, which upon interaction with an oxidoreductase and an oxidizing agent, becomes oxidized or otherwise activated and which in its oxidized or otherwise activated state provides a more powerful antimicrobial effect than could be obtained by the oxidoreductase and the oxidizing agent alone.

In the context of the invention the term "water based paint" is to be construed as a composition usually comprising solid coloring matter dissolved or dispersed in a liquid vehicle comprising at least 10% water, organic solvent and/or oils, which when spread over a surface, dries to leave a thin colored, decorative and/or protective coating. In the context of the invention this term is however also thought to encompass water based enamel, lacquer and/or polish compositions.

In the context of the invention the term "oxidizing agent" is to be construed as a chemical or biological compound, which may act as an electron acceptor and/or oxidant. The oxidizing agent may mediated by an oxidoreductase catalyst oxidize an electron donor substrate, e.g. an enhancer (c.f. above).

In the context of the invention the term "preservation and/or conservation" is to be construed as preventing and/or inhibiting microbial growth such as fungal and/or bacterial growth in the medium, which is preserved and/or conserved.

In the context of the invention the term "disinfection" is to be construed as killing microbial cells such as fungal and/or bacterial cells in the medium, which is disinfected.

In the context of the invention the term "solvent" is to be construed as an organic liquid, which usually is partly or competely water immiscible.

In the context of the invention the term "viscosifier" is to be construed as a compound which when added to a liquid medium increases the viscosity of said liquid medium.

In the context of the invention the term "pigment" is to be construed as a colored compound, which when added to a composition may provide the composition with a desired color.

In the context of the invention the term "dispersant" is to be construed as a compound, which when added to a heterogenous liquid of a solid-liquid mixture improves the distribution of solid particles in the liquid, i.e. the dispersant helps keeping solid particles suspended in the liquid.

In the context of the invention the term "foam suppresser" is to be construed as a compound which when added to a liquid prevents and/or inhibits the formation of foam when said liquid is stirred, skaked, mixed, aerated or otherwise agitated thereby gases to enter the liquid.

In the context of the invention the term "siccatives" is to be construed as water and/or moisture absorbing compounds or drying agents.

In the context of the invention the term "binder" is to be construed as the substance in the water based paint which, when the paint has been applied to a suitable surface and dried up, constitutes the continuous usually polymeric and adhesive matrix in which other paint constituents such as pigments are distributed immobilized.

Oxidoreductases

The oxidoreductase in the context of the present invention may be any oxidoreductase or combination of different oxidoreductases or combination of oxidoreductases with other enzymes, which facilitates the disinfection and/or preservation and/or conservation effect in a water based paint. Accordingly, when reference is made to "an oxidoreductase" this will in general be understood to include combinations of one or more oxidoreductases.

It is to be understood that oxidoreductase variants (produced, for example, by recombinant techniques) are included within the meaning of the term "oxidoreductase".

The enzyme classification employed in the present specification with claims is in accordance with *Recommendations (1992) of the Nomenclature Committee of the International Union of Biochemistry and Molecular Biology*, Academic Press, Inc., 1992.

Accordingly the types of oxidoreductases which may appropriately be applied for preservation and/or conservation of a water based paint include oxidoreductases (EC 1.–.–.–).

Preferably oxidoreductases in the context of the invention are any peroxidase belonging to the classification group EC 1.11.1.–, any laccase belonging to EC 1.10.3.2, any catechol oxidase belonging to EC 1.10.3.1, any bilirubin oxidase belonging to EC 1.3.3.5 or any monophenol monooxygenase belonging to EC 1.14.99.1 or any oxidase belonging to EC 1.3.3.–.

Laccase and Laccase Related Enzymes

Preferred laccase enzymes and/or laccase related enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinus*, e.g., *C. cinereus, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyprous*, e.g., *P. pinsitus, Phlebia*, e.g., *P. radita* (WO 92/01046), or *Coriolus*, e.g., *C. hirsutus* (JP 2-238885).

Suitable examples from bacteria include a laccase derivable from a strain of *Bacillus*.

A laccase derived from *Coprinus, Myceliophthora, Polyporus, Scytalidium* or *Rhizoctinia* is preferred; in particular a laccase derived from *Coprinus cinereus, Myceliophthora thermophila, Polyporus pinsitus, Scytalidium thermophilum* or *Rhizoctonia solani*.

The laccase or the laccase related enzyme may furthermore be one which is producible by a method comprising cultivating a host cell transformed with a recombinant DNA vector which carries a DNA sequence encoding said laccase as well as DNA sequences encoding functions permitting the expression of the DNA sequence encoding the laccase, in a culture medium under conditions permitting the expression of the laccase enzyme, and recovering the laccase from the culture.

Determination of Laccase Activity (LACU)

Laccase activity, preferable laccases derivable from a strain of *Polyporus*, may be determined from the oxidation of syringaldazin under aerobic conditions. The violet colour produced is photometered at 530 nm. The analytical conditions are 19 mM syringaldazin, 23 mM acetate buffer, pH 5.5, 30° C. 1 min. reaction time.

1 laccase unit (LACU) is the amount of enzyme that catalyses the conversion of 1.0 µmole syringaldazin per minute at these conditions.

Determination of Laccase Activity (LAMU)

Laccase activity may be determined from the oxidation of syringaldazin under aerobic conditions. The violet colour produced is measured at 530 nm. The analytical conditions are 19 mM syringaldazin, 23 mM Tris/maleate buffer, pH 7.5, 30° C., 1 min. reaction time.

1 laccase unit (LAMU) is the amount of enzyme that catalyses the conversion of 1.0 µmole syringaldazin per minute at these conditions.

The use of Laccases for preservation and/or conservation of paints benefits from the fact that laccases may utilize abundant molecular oxygen directly as oxidant.

Peroxidases and Compounds Possessing Peroxidase Activity

Compounds possessing peroxidase activity may be any peroxidase enzyme comprised by the enzyme classification (EC 1.11.1.7), or any fragment derived therefrom, exhibiting peroxidase activity. In the context of this invention, compounds possessing peroxidase activity comprise peroxidase enzymes and peroxidase active fragments derived from cytochromes, haemoglobin or peroxidase enzymes.

Preferably, the peroxidase employed in the method of the invention is producible by plants (e.g. horseradish or soybean peroxidase) or microorganisms such as fungi or bacteria.

Some preferred fungi include strains belonging to the subdivision *Deuteromycotina*, class *Hyphomycetes*, e.g., *Fusarium, Humicola, Trichoderma, Myrothecium, Verticillum, Arthromyces, Caldariomyces, Ulocladium, Embellisia, Cladosporium* or *Dreschlera*, in particular *Fusarium oxysporium* (DSM 2672), *Humicola insolens, Trichoderma resii, Myrothecium verrucaria* (IFO 6113), *Verticullum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision *Basidiomycotina*, class *Basidiomycetes*, e.g., *Coprinus, Phanerochaete, Coriolus* or *Trametes*, in particular *Coprinus cinereus f. microsporus* (IFO 8371), *Coprinus macrorhizus, Phanerochaete chrysosporium* (e.g. NA-12) or *Trametes* (previously called *Polyporus*), e.g., *T. versicolor* (e.g. PR4 28-A).

Further preferred fungi include strains belonging to the subdivision *Zygomycotina*, class *Mycoraceae*, e.g., *Rhizopus* or *Mucor*, in particular *Mucor hiemalis*.

Some preferred bacteria include strains of the order *Actinomycetales*, e.g. *Streptomyces spheroides* (ATTC 23965), *Streptomyces thermoviolaceus* (IFO 12382) or *Sreptoverticillum verticillium ssp. verticillium*.

Other preferred bacteria include *Bacillus pumilus* (ATCC 12905), *Bacillus stearothermophillus, Rhodobacter sphaerodies, Rhodomonas palustri, Streptococcus lactics, Pseudomonas purrocinia* (ATCC 15958) or *Pseudomonas fluorescens* (NRRL B-11).

Further preferred bacteria include strains belonging to *Myxococcus*, e.g., *M. virescens*.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a *Coprinus sp.*, in particular *C. macrorhizue* or *C. cinereus* according to WO 92/16634.

Also haloperoxidases such as chromo-, bromo- and/or iodoperoxidases are suitable for preserving a paint according to the invention. Haloperoxidases form a class of enzymes which are able to oxidize halides (Cl-, Br-, I-) in the presence of hydrogen peroxide or a hydrogen peroxide generating system to the corresponding hypohalous acids accordint to:

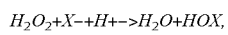

wherein X- is a halide and HOX is a hypohalous acid

If a convenient nucleophilic acceptor is present, a reaction will occur with HOX and a halogenated compound will be formed.

There are three types of haloperoxidases, classified according to their specificity for halide ions: Chloroperoxidases (E.C. 1.11.1.10) which catalyse formation of hypochlorit from chloride ions, hypo-bromit from bromide ions and hypo-iodit from iodide ions; Bromoperoxidases which catalyse formation of hypo-bromit from bromide ions and hypo-iodit from iodide ions; and iodoperoxidases (E.C. 1.11.1.8) which solely catalyze the formation of hypoiodit from iodide ions. However, hypoidit underoes spontanous disproportionation to iodine and thus, iodine is usually the observed product of the reaction. These hypo-halit compounds may subsequently react with other compounds forming halogenated compounds.

Haloperoxidases have been isolated from various organisms: mammals, marine animals, plants, algae, a lichen, fungi and bacteria (for reference see Biochimica et Biophysica Acta 1161, 1993, pp. 249–256). It is generally accepted that haloperoxidases are the enzymes responsible for the formation of halogenated compounds in nature, although other enzymes may be involved.

Haloperoxidases have been isolated from many different fungi, in particular from the fungus group dematiaceous hyphomycetes, such as *Calariomyces*, e.g., *C. fumago, Alternaria, Curvularia*, e.g., *C. verruculosa* and *C. inaequalis, Drechslera, Ulocladium* and *Botrytis* (see U.S. Pat. No. 4,937,192).

According to the present invention a haloperoxidase obtainable from *Curvularia*, in particular *C. verruculosa* is preferred such as *C. verruculosa* CBS 147.63 or *C. verruculosa* CBS 44.70. Curvularia haloperoxidase and recombinant production hereof is described in WO 97/04102.

Haloperoxidase have also been isolated from bacteria such as *Pseudomonas*, e.g., *P. pyrrocinia* (for reference see The Journal of Biological Chemistry 263, 1988, pp. 13725–13732) and *Streptomyces*, e.g., *S. aureofaciens* (for reference see Structural Biology 1, 1994, pp. 532–537).

Bromide peroxidase has been isolated from algae (see U.S. Pat. No. 4,937,192).

In a preferred embodiment the haloperoxidase is derivable from *Curvularia* sp., in particular *C. verruculosa* and *C. inaequalis*.

In a preferred embodiment the haloperoxidase is a vanadium haloperoxidase derivable from a strain of *Curvularia inaequalis* such *C. inaequalis* CBS 102.42 as described in WO 95/27046, e.g. a vanadium haloperoxidase encoded by the DNA sequence of WO 95/27046, FIG. 2 all incorporated by reference.

In another preferred embodiment the haloperoxidase is a vanadium haloperoxidase derivable from a strain selected from *Drechslera hartlebii, Dendryphiella salina, Phaeotrichoconis crotalarie* and *Geniculosporium* sp. The vanadium haloperoxidase is more preferably derivable from *Drechslera hartlebii* (DSM Acc. No. DSM 13444), *Dendryphiella salina* (DSM Acc. No. DSM 13443), *Phaeotrichoconis crotalarie* (DSM Acc. No. DSM 13441) and *Geniculosporium* sp. (DSM Acc. No. DSM 13442) such as described in the co-pending Danish patent applications PA2000 00628, PA 2000 00627, PA2000 00625 and PA2000 00626 all incorporated by reference.

Determination of Peroxidase Activity (POXU)

One peroxidase unit (POXU) is the amount of enzyme which under the following conditions catalyze the conversion of 1 μmole hydrogen peroxide per mininute: 0.1 M phosphate buffer pH 7.0, 0.88 mM hydrogen peroxide, 1.67 mM 2,2'-azino-bis(3-ethylbenzothiazoline-6-sulfonate) (ABTS) and 30° C.

The reaction is followed for 60 seconds (15 seconds after mixing) by the change in absorbance at 418 nm, which should be in the range 0.15 to 0.30.

For calculation of activity is used an absorption coefficient of oxidized ABTS of 36 mM$^1$ cm$^1$ and a stoichiometry of one μmole $H_2O_2$ converted per two μmole ABTS oxidized.

A suitable amount of oxidoreductase to be incorporated in a water based paint composition or a drilling fluid will generally depend on the oxidoreductase, but typically an amount between about 0.01 to about 1000 mg enzyme protein per liter composition, preferably 0.1–100 mg/l, e.g. 0.1–50 mg/l or 0.2–10 mg/ml will be suitable.

Water Based Paint Compositions Preserved by Oxidoreductases

As defined vide supra a water based paint which may be disinfected and/or preserved and/or conserved by an oxidoreductase is a composition comprising a solid matter dissolved or dispersed in a liquid vehicle comprising an oxidoreductase and at least 10% water, which when spread over a surface, dries up to leave a thin colored, decorative and/or protective coating. Paints encompassed by the invention includes paints suitable for indoors use and paints for outdoors uses as well as water based wood impregnation paints.

As mention vide supra the invention provides in one aspect a preserved water based paint comprising an oxidoreductase, an oxidizing agent, at least 10% water and a binder.

Usually water constitutes 10–90% w/w of the total composition, preferably 20–80% w/w such as 30–70% w/w or 30–50% w/w of the total composition.

The binder which may be used in the paint composition include acrylic compounds such as acrylstyrene, acrylate or acylate copolymers. Also a binder such as polyvinylacetate or other such polymers and/or copolymers thereof may be used. Also any suitable combination of binders may be employed. Binders may preferable consitute 5–50% w/w of the total paint composition, preferably 5–40% w/w such as 10–30% w/w.

A suitable choice of oxidizing agent depends on the type of oxidoreductase. If the oxidoreductase is a laccase or a laccase related enzyme the oxidizing agent may be molecular oxygen available from the atmosphere. Usually oxygen from the atmosphere is sufficient but the paint composition may also be saturated with oxygen e.g. aeration if necessary. A particular advantageous feature of using laccases for preservation and/or conservation is that the oxidizing agent, namely molecular oxygen, is abundantly available from the atmosphere, so that when e.g. a paint composition is exposed to microbial activity from the environment, e.g. by opening a sealed container in which paint compositions are usually stored, access to the composition is also provided for the oxidizing agent which initiates and/or boosts the disinfecting and/or preserving and/or conserving activity of the laccase preservation system.

If the oxidoreductase is a peroxidase or a compound having peroxidase activity the oxidizing agent is suitably a peroxo compound in particular hydrogen peroxide or a source of hydrogen peroxide (a hydrogen peroxide precursor) which provide for in situ production of hydrogen peroxide, e.g., percarbonate or perborate compounds or a peroxycarboxylic acid or a salt thereof, or it may be a hydrogen peroxide generating enzyme system, such as an oxidase and its substrate. Useful oxidases may be, a glucose oxidase, a glycero oxidase or an amino acid oxidase. An example of an amino acid oxidase is given in WO 94/25574.

It may be advantageous to use enzymatically generated hydrogen peroxide, since this source results in a relatively low concentration of hydrogen peroxide under the biologically relevant conditions. Low concentrations of hydrogen peroxide result in an increase in the rate of peroxidase-catalysed reaction. The oxidizing agent in this case may suitably be present in the preserved paint or drilling fluid composition of the invention in an amount corresponding to levels from 0.001–500 mM, particularly to levels from 0.01–100 mM such as 0.01–25 mM.

A water based paint compositions of the invention usually also comprise other components such as solvents, pigments, fillers, viscosifiers, dispersants, foam suppressors, siccatives, and/or enhancers.

Solvent(s) such as white spirit, glycols such as butyl glycol, butyldiglycol, propylene glycol, tripropyleneglycol-n-butylether, ethylene glycol, other alcohols such as texanol may be employed. Also ammonia may be used as a solvent. Solvents may be applied alone or in any suitable combination. Solvents in water based paints are typically included in less amounts than water and may preferably constitute 0–50% w/w of the paint composition. A more preferred range of solvents is 0–20% w/w, e.g. 0–10% w/w, but in most cases a water based paint composition comprises 2–10% w/w solvent(s).

Pigments may suitably be titanium dioxide optionally in combination with other pigments depending on which color is intended for the water based paint. The pigments usually consitute 0.5–50% w/w of the composition, preferably 1–40% w/w, such as 5–35% w/w or 10–30% w/w.

Fillers, which may be used in the paint composition include inorganic compounds which are preferably substantially water insoluble such as calcium carbonate, talc, aluminum silicates and/or dolomite or combinations thereof. The fillers usually constitutes 2–40% w/w of the total composition, preferably 5–30% w/w e.g. 15–30% or 2–30% w/w.

Viscosifiers, which may be used in the paint composition include polyacrylates, polyurethane or cellulose derivatives such as hydroxyethylcellulose or suitable combination of such viscosifiers. The viscosifiers may constitute about 0–5% w/w of the total paint composition, preferable about 0–2% w/w such as 1–2% w/w.

Different dispersants may be used in the paint composition. Dispersant may include natural dispersants such as proteins such as lecithine e.g. extracted from soy or another natural source or the dispersant may be organic such as polyglycolethers or -esters, octyl- or nonylphenolethoxylates or the dispersant may be inorganic such as tripolyphosphates or it may be a combination of inorganic and organic compounds such as acrylic acid and sodiumhydroxide. Any suitable combinations of such dispersants may also be employed. The dispersant may constitute 0–5% w/w of the total paint composition preferably 0–3% w/w, e.g. 0.5–2% w/w.

Foam suppressers, which may be used in the paint composition include mineral oils, silicone oils and fatty acid esters or any suitable combination of such foam suppressors. The foam suppressor may constitute 0–5% w/w of the total paint composition preferably 0–3% w/w such as 0.1–5% w/w or 0.2–0.5% w/w.

Siccatives, which may be used in the paint composition include metal salts or organic acids such as cobaltoctoate, zirconiumctoate, calciumnaphthenate or zinknaphtenat or any suitable combination thereof. The siccatives may constitute 0–5% w/w of the total paint composition preferably 0–2% such as 0–1% w/w or 0.1–1% w/w or 0.1–0.5% w/w.

Enhancers, which may be used in the paint composition to enhance the antimicrobial effect include organic enhancers and inorganic enhancers. Various organic enhancers acting as electron donors for oxidoreductases for various purposes are known to the art (e.g. from WO 94/12620, WO 94/12621, WO 95/01626 and WO 96/00179) and may suitably be employed in accordance with this invention. It is to be understood that it is preferred that the paint composition of the invention comprises at least one enhancer. The invention encompasses also paint compositions comprising two or more different enhancers, because different enhancers preserve the composition against different microorganisms with different potency. Thus by combining enhancers it is possible to optimize preservation of the paint composition.

One group of preferred organic enhancers is phenolic compounds (alkylsyringates) of the formula:

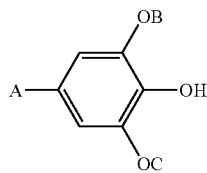

Formula I wherein the letter A in said formula denotes be a group such as —D, —CH=D, —CH=CH—CH=CH—D, —CH=N—D, —N=N13 D, or —N=CH—D, in which D is selected from the group consisting of —CO—R, —SO$_2$—E, —N—XY, and —N$^-$—XYZ, in which E may be —H, —OH, —R, or —OR, and X and Y and Z may be identical or different and selected from —H and —R; R being a $C_1$–$C_{16}$ alkyl, preferably a $C_1$–$C_8$ alkyl, which alkyl may be saturated or unsaturated, branched or unbranched and optionally substituted with a carboxy, sulpho or amino group; and B and C may be the same or different and selected from $C_mH_{2m+1}$, where m=1, 2, 3, 4 or 5.

In the above mentioned formula A may be placed meta to the hydroxy group instead of being placed in the para-position as shown.

In particular embodiments of the invention the enhancer is selected from the group having the formula:

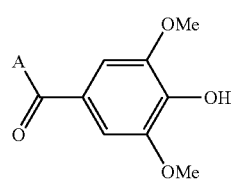

Formula II in which A is a group such as —H, —OH, —CH$_3$, —OCH$_3$, —O(CH$_2$)$_n$CH$_3$, where n=1, 2, 3, 4, 5, 6, 7 or 8.

Such enhancers may suitably be present in the paint composition in amount between 0.00001–500 mM, preferably 0.0001–5 mM, e.g. 0.001–0.050 mM.

Another preferred group of well performing organic enhancers comprises a —CO NOH— group and having the following formula:

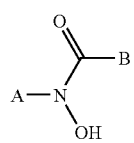

Formula III in which A is:

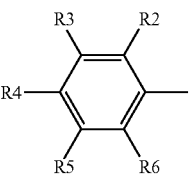

Formula IV and B is the same as A, or B is H, or C1–C16 branched or unbranched alkyl wherein said alkyl may contain hydroxy, ether or ester groupgs, and R2, R3, R4, R5 and R6 are H, OH, NH2, COOH, SO3H, C1–C12 branched or unbranched alkyl, acyl, NO2, CN, Cl, CF3, NOH—CO-phenyl, C1–C6—CO-NOH—A, CO—NOH—A, COR12, phenyl-—CO—NOH—A, OR7, NR8R9, COOR10, or NOH—CO—R11, wherein R7, R8, R9, R10 and R11 are C1–C12 branched or unbranched alkyl or acyl. Whitin this group of enhancers particularly preferred enhancers are selected from the group consisting of 4-nitrobenzoic acid-N-hydroxyanilide; 4-methoxybenzoic acid N-hydroxyanilide; M,N'-dihydroxy-N,N'-diphenylterephthalamide; decanoic acid-N-hydroxyanilide; N-hydroxy-4-cyanoacetanilide; N-hydroxy-4-acetylacetanilide; N-hydroxy-4-hydroxyacetanilide; N-hydroxy-3-(N'-hydroxyacetamide)acetanilide; 4-cyanobenzoic acid-N-hydroxyanilide; N-hydroxy-4-nitroacetanilide; and N-hydroxyacetanilide.

The enhancer may also be one of the compounds disclosed in WO 96/18770 such as N-hydroxy compounds, in particular aliphatic, cycloaliphatic, heterocyclic or aromatic compounds containing NO—, N(OH)—, or N(OH) (R$_1$), especially N-hydroxy benzotriazol (HOBT), Violuric acid, or N-hydroxyacetanilide (HAA).

In a preferred embodiment of the invention the enhancer is a compound of the general formula (V):

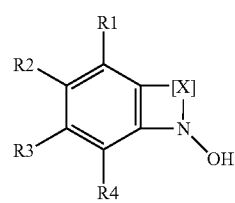

Formula V wherein $R^1$, $R^2$, $R^3$, $R^4$ are individually selected from the group consisting of hydrogen, halogen, hydroxy, formyl, carboxy and salts and esters thereof, amino, nitro, $C_1$–$C_{12}$ alkyl, $C_1$–$C_6$ alkoxy, carbonyl ($C_1$–$C_{12}$ alkyl), aryl, in particular phenyl, sulpho, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl($C_1$–$C_{12}$ alkyl, aryl, in particular phenyl, sulpho, aminosulfonyl, carbamoyl, phosphono, phosphonooxy, and salts and esters thereof, [X] represents a group selected from (—N=N—, (N=CR$^6$—)$_m$, —CR$^6$=N—)$_m$, (CR$^6$=CR$^7$—)$_m$, (—CR$^6$=N—NR$^7$—), (—N=N—CH$^6$), (—N=CR$^6$—NR$^7$), (—N=CR$^6$—CHR$^7$—), (—C$^6$=N—CHR$^7$), (—CR$^6$=CR$^7$—NR$^8$—), and (—CR$^6$—CR$^7$—CHR$^8$—), wherein R$^6$, R$^7$, and R$^8$ independently of each other are selected from H, OH, $NH_2$, COOH, $SO_3H$, $C_{1-6}$-alkyl, $NO_2$, CN, Cl, Br, F, $CH_2OCH_3$, $OCH_3$, $COOCH_3$; and m is 1 or 2.

In a more preferred embodiment of the invention the enhancer is a compound of the general formula (VI):

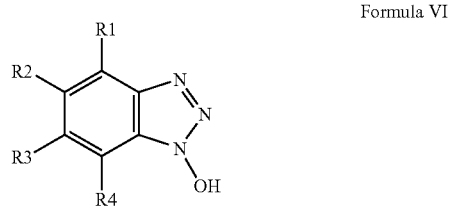

Formula VI wherein $R^1$, $R^2$, $R^3$, $R^4$ are individually selected from the group consisting of hydrogen, halogen, hydroxy, formyl, carboxy and salts and esters therof, amino, nitro, $C_1$–$C_{12}$ alkyl, $C_1$–$C_6$ alkoxy, carbonyl ($C_1$–$C_{12}$ alkyl), aryl, in particular phenyl, sulpho, aminosulfonyl, carbamoyl, phosphono, phosphonooxy, and salts and esters thereof, wherein the $R^1$, $R^2$, $R^3$, $R^4$ may be substituted with $R^5$, wherein $R^5$ represents hydrogen, halogen, hydroxy, formyl, carboxy and salts and esters thereof, amino, nitro, $C_1$–$C_{12}$ alkyl, $C_1$–$C_6$ alkoxy, carbonyl ($C_1$–$C_{12}$ alkyl), aryl, in particular phenyl, sulpho, aminosulfonyl, carbamoyl, phosphono, phosphonooxy, and salts and esters thereof.

The enhancer may also be a salt or an ester of formula V or VI.

Further preferred enhancers are oxoderivatives and N-hydroxy derivatives of heterocyclic compounds and oximes of oxo- and formyl-derivatives of heterocyclic compounds, said heterocyclic compounds including five-membered nitrogen-containing heterocycles, in particular pyrrol, pyrazole and imidazole and their hydrogenated counterparts (e.g. pyrrolidine) as well as triazoles, such as 1,2,4-triazole; six-membered nitrogen-containing heterocycles, in particular mono-, $d_1$- and triazinances (such as piperidine and piperazine), morpholine and their unsaturated counterparts (e.g. pyridine and pyrimidne); and condensed heterocycles containing the above heterocycles as substructures, e.g. indole, benzothiazole, quinoline and benzoaepine.

Examples of preferred enhancers from these classes of compounds are pyridine aldoximes; N-hydroxypyrrolidinediones such as N-hydroxysuccinimide and N-hydroxyphthalimide; 3,4-dihydro-3-hydroxybenzo[1,2,3]triazine-4-one; formaldoxime trimer (N,N',N''-trihydroxy-1,3,5-triazinane); and violuric acid (1,3-diazinane-2,4,5,6-tetrone-5-oxime).

Still further enhancers which may be applied in the invention include oximes of oxo- and formyl-derivatives of aromatic compounds, such as benzoquinone dioxime and salicylaldoxime (2-hydroxybenzaldehyde oxime), and N-hydroxyamides and N-hydroxyanilides, such as N-hydroxyacetanilide.

Preferred enhancers are selected from the group consisting of 1-hydroxybenzotriazole; 1-hydroxybenzotriazole hydrate; 1-hydroxybenzotriazole sodium salt; 1-hydroxybenzotriazole potassium salt; 1-hydroxybenzotriazole lithium salt; 1-hydroxybenzotriazole ammonium salt; 1-hydroxybenzotriazole calcium salt; 1-hydroxybenzotriazole magnesium salt; and 1-hydroxybenzotriazole-6 sulphonic acid.

A particularly preferred enhancer is 1-hydroxybenzotriazole.

All the specifications of N-hydroxy compounds above are understood to include tautomeric forms such as N-oxides whenever relevant.

In particular, the enhancer of the invention may be the corresponding N-oxyl free radical to any of the compounds disclosed in WO 96/18770 such as TEMPO (2,2,6,6-tetramethylpiperidinoxyl).

The organic enhancers may suitably be present in the paint composition in concentrations from 1 to 1000 μM, preferably from 5 to 500 μM.

Inorganic enhancers may also be relevant. Especially when using haloperoxidases for preservation of water based paint or drilling fluid compositions presence of inorganic halide ions such as chloride, bromide and/or iodide may enhance the antimicrobial effect of the haloperoxidase. Suitable ranges of chloride ions are 0.05–500 mM and suitable ranges of bromide and/or iodide ions are 0.01–100 mM.

We have further observed that an improved anti-microbial or preservation effect may be obtained using an ammonium enhancer, preferably in combination with a halide enhancer or an organic enhancer. The ammonium enhancer may be compounds of the formula:

Formula VII wherein the substituent groups R1 and R2 may be identical or different. R1 and R2 may suitably be any of the following groups: hydrogen, halide, sulphate, phenyl, a straight or branched chain alkyl having from 1 to 14 carbon atoms, or a substituted straight or branched alkyl group having from 1 to 14 carbon atoms where the substituent group is located at $C_1$–$C_{14}$ and represent any of the following radicals: hydroxy, halogen, formyl, carboxy, carboxy esters, carboxy salts, carbamoyl, sulfo, sulfo esters, sulfo salts, sulfamoyl, nitro, amino, phenyl, $C_1$–$C_5$-alkoxy, carbonyl-$C_1$–$C_5$-alkyl, aryl-$C_1$–$C_5$-alkyl. Where R1 and/or R2 includes groups selected from carbamoyl, sulfamoyl, and amino groups these groups may furthermore be unsubstituted or substituted once or twice with a substitutent group R3, where R1 and/or R2 includes a phenyl group it may furthermore be unsubstituted or substituted with one or more substituent groups R3. Where R1 and/or R2 includes groups selected from $C_1$–$C_5$-alkoxy, carbonyl-$C_1$–$C_5$-alkyl, and aryl-$C_1$–$C_5$-alkyl these groups may be saturated or unsaturated, branched or unbranched, and may furthermore b unsubstituted or substituted with one or more substituent groups R3. R3 represents any of the following groups: halogen, hydroxy, formyl, carboxy, carboxy esters, carboxy salts, carbamoyl, sulfo, sulfo esters, sulfo salts, sulfamoyl, nitro, amino, phenyl, aminoalkyl, piperidino, piperazinyl, pyrrolidin-1-yl, $C_1$–$C_5$-alkyl, $C_1$–$C_5$-alkoxy. Where R3 includes groups selected from carbamoyl, sulfamoyl, and amino these groups may furthermore be unsubstituted or substituted once or twice with hydroxy, $C_1$–$C_5$-alkyl, $C_1$–$C_5$-alkoxy. Where R3 includes phenyl this group may futhermore be substituted with one or more of the following groups: halogen, hydroxy, amino, formyl, carboxy, carboxy esters, carboxy salts, carbamoyl, sulfo, sulfo esters, sulfo salts, and sulfamoyl. Where R3 includes groups selected from $C_1$–$C_5$-alkyl, and $C_1$–$C_5$- alkoxy these groups may furthermore be saturated or unsaturated, branched or unbranched, and may furthermore be substituted once or twice with any of the following radicals: halogen, hydroxy, amino, formyl, carboxy, carboxy esters, carboxy salts, carbamoyl, sulfo, sulfo esters, sulfo salts, and sulfamoyl, R1 and R2 may also suitably together a group —B—, in which B represents any of the following groups: (—CHR3—N=N—), (—CH=CH—)$_n$ or (—CH=N—)$_n$ in which groups n-represents an integer of from 1 to 3 and R3 is a substituent group as defined, supra. (It is to be understood that if the above mentioned formula comprises two or more R3-substituent groups, these R3-substituent groups may be the same or different).

As used herein, the ammonium enhancer may be in their cationic form.

In a preferred embodiment R1 is hydrogen.

In another preferred embodiment R1 is hydrogen and R2 is an alcohol (amino alcohol), e.g., ethanol amine.

In a further preferred embodiment the ammonium enhancer is an ammonium salt, i.e. any ammonium salt known in the art: e.g., diammonium sulphate, ammonium chloride, ammonium bromide, or ammonium iodide.

The ammonium enhancer may suitably be present in the paint composition of the invention in a concentration corresponding to an ammonium concentration in the range of from 0.01–1000 mM, preferably in the range of from 0.05–500 mM.

Water Based Fluid Compositions for use in the Oil and Gas Industry

As mentioned, supra, the invention also relates to a preserved and/or conserved water based fluid composition selected from the group consisting of drilling fluids, completion fluids, fracturing fluids, injection fluids, blocking gels and workover fluids said fluids comprising an oxidoreductase, an oxidizing agent and a biopolymer. In the oil and gas industry a range of different fluids are used during the course of drilling for and production of fossil oil and/gas. The fluids often contain biopolymers or other organic components to give the fluid e.g. viscosifying or gelling properties. To prevent microbial degradation of these components, biocides such as glutaraldehyde and different oxidisers are typically added to the fluid system. Instead of the traditional biocides used in this industry, an enzyme based preservation system may be used in accordance with the invention.

The biopolymer may be based on starches, such as corn, potato, rice or other grain starches, celluloses or derivatives thereof, guar gum and/or xanthan gum, which are excellent sbustrates for a range of different microorganisms. If the polymer structure is degraded by microbial attack the polymer looses its properties which can be detrimental in a process where the biopolymer secures the right fluid or gel properties. Undesired polymer degradation may in the worst case cause safety problems while a less hazardous consequence may be failure of the drilling operation and thereby loss of valuable time and financial resources. The fluids which usually requires addition of biocides includes but are not limited to drilling fluids, completion fluids, fracturing fluids, injection fluids, blocking gels and workover fluids. Other fluid types used in the oil and gas industry which are not specifically mentioned above but which contan conventional biocides is also encompassed by the invention.

When preserving such fluids the oxidoreductase enzymes and oxidizing agent as described, vide supra, may suitably be employed. Further it may be desirable to include enhancers as described, supra, in the fluid composition.

Addition of the oxidoreductase preservation systems can suitably be carried out during the mixing process of the different fluid types, which may take place at ambient temperature and of importance when using laccase types of enzymes in the presence of atmospheric oxygen. This means that the fluid is sanitised during mixing, before being pumped down the bore hole.

The invention is illustrated by the following unlimiting examples of oxidoreductase preserved water based paint composition and oxidoreductase preserved drilling fluid compositions.

EXAMPLE 1

The following example of an enzymatically preserved water based paint suitable for indoors use was prepared:

| Compound | Suitable Types | Amount |
| --- | --- | --- |
| Binder | Acryl-styren<br>Acrylat<br>Acrylat copolymers<br>polyvinylacetate | 10–30% w/w |
| Pigments | TiO$_2$<br>Other pigments | 10–25% w/w |
| Solvent | White spirit<br>Butylglycol<br>Butyldiglycol<br>Propyleneglycol<br>ethyleneglycol<br>texanol<br>Ammonia | 0–2% w/w |
| Filler | calcium carbonate<br>Talc<br>Aluminumsilicate<br>dolomite | 15–30% w/w |
| Viscosifier | hydroxyethylcellulose<br>polyacrylates<br>polyurethaner | 0.1–2% w/w |
| Dispersant | Soy lecithin<br>acrylic acid/sodium hydroxide<br>polyglycolethers or -esters<br>octyl- or<br>nonylphenolethoxylates<br>tripolyphosphate | 1–3% w/w |
| Foam suppresser | mineral oil<br>silicone oil<br>fatty acid esters | 0.2–0.5% w/w |
| Siccatives | Cobaltoctoate<br>Zirkonium octoate<br>calciumnaphtenate<br>zinknaphtenate | 0.1–0.5% w/w |
| Enhancer | halide salts<br>alkylsyringate<br>hydroxyanilide compounds<br>diphenylterephthalamide<br>compounds<br>acetanilide compounds | 0.001–1 mM |
| Enzymes | Laccase<br>peroxidase<br>haloperoxidase<br>oxidase | 0.1–100 mg/l |
| Oxidizing agent | Hydrogenperoxide<br>sodium perborate<br>sodium percabonate<br>peroxycarboxylic acid<br>Oxygen | 0.01–100 mM |
| Water | | 30–50% w/w |

EXAMPLE 2

The following example of an enzymatically preserved water based paint suitable for outdoors use was prepared:

| Compound | Suitable Types | Amount |
| --- | --- | --- |
| Binder | Acryl-styren<br>Acrylat<br>Acrylat copolymers<br>polyvinylacetate | 20–30% w/w |
| Pigments | TiO₂<br>Other pigments | 20–25% w/w |
| Solvent | White spirit<br>Butylglycol<br>Butyldiglycol<br>Propyleneglycol<br>ethyleneglycol<br>texanol<br>tripyleneglycol-n-butylether<br>Ammonia | 2–10% w/w |
| Filler | Talc<br>Aluminumsilicate<br>dolomite | 5–10% w/w |
| Viscosifier | hydroxyethylcellulose<br>polyacrylates<br>polyurethaner | 0.1–2% w/w |
| Dispersant | Soy lecithin<br>acrylic acid/sodium hydroxide<br>polyglycolethers or -esters<br>octyl- or<br>nonylphenolethoxylates<br>tripolyphosphate | 0.5–1.5% w/w |
| Foam suppresser | mineral oil<br>silicone oil<br>fatty acid esters | 0.1–0.5% w/w |
| Enhancer | halide salts<br>alkylsyringate<br>hydroxyanilide compounds<br>diphenylterephthalamide<br>compounds<br>acetanilide compounds | 0.001–1 mM |
| Enzymes | Laccase<br>peroxidase<br>haloperoxidase<br>oxidase | 0.1–100 mg/l |
| Oxidizing agent | Hydrogenperoxide<br>sodium perborate<br>sodium percabonate<br>peroxycarboxylic acid<br>Oxygen | 0.01–100 mM |
| Water | | 40–50% w/w |

EXAMPLE 3

The following example of an enzymatically preserved water based paint suitable for outdoors wood protection/impregnation:

| Compound | Suitable Types | Amount |
| --- | --- | --- |
| Binder | Acrylat<br>Acrylat copolymers | 20–30% w/w |
| Pigments | TiO₂<br>Other pigments | 20–25% w/w |
| Solvent | White spirit<br>Butylglycol<br>Butyldiglycol<br>Propyleneglycol<br>ethyleneglycol<br>texanol<br>tripyleneglycol-n-butylether<br>Ammonia | 2–10% w/w |
| Filler | Talc<br>Aluminumsilicate<br>dolomite | 5–10% w/w |
| Viscosifier | hydroxyethylcellulose<br>polyacrylates<br>polyurethaner | 1–2% w/w |
| Dispersant | Soy lecithin<br>acrylic acid/sodium hydroxide<br>polyglycolethers or -esters<br>octyl- or<br>nonylphenolethoxylates<br>tripolyphosphate | 1–2% w/w |
| Foam suppresser | mineral oil<br>silicone oil<br>fatty acid esters | 0.1–0.5% w/w |
| Siccative | Cobaltoctoate<br>Zirkonium octoate<br>calciumnaphtenate<br>zinknaphtenate<br>acetanilide compounds | 0–0.5% w/w |
| Enhancer | halide salts<br>alkylsyringate<br>hydroxyanilide compounds<br>diphenylterephthalamide<br>compounds<br>acetanilide compounds | 0.001–1 mM |
| Enzymes | Laccase<br>peroxidase<br>haloperoxidase<br>oxidase | 0.1–100 mg/l |
| Oxidizing agent | Hydrogenperoxide<br>sodium perborate<br>sodium percabonate<br>peroxycarboxylic acid<br>Oxygen | 0.01–100 mM |
| Water | | 40–50% w/w |

EXAMPLE 3

The preservative effect of Myceliophthora laccase (Novo Nordisk A/S) with methylsyrignate as enhancer was evaluated by addition of the enzyme system to paint. The test is an accelerated storage test, where the enzyme system is added to un-preserved paint. The test paint was made from the following ingrediens (% W/V); water (27%), Foamaster DNH-1 (0.1%) Dispex N40 (0.4%), Celacol HPM 15000DS (0.4%), Ammonia 0.88 (0.03%), Tiona 535 (15%), Talc IT Extra (5%), Satintone W (5%), Microdol H400 (13%), Latex (acryl) (33.5%), Tilcom AT23 (0.5%). The enzyme system was added to the test paint and aged for 14 days at 45° C., after which the paint is inoculated with a mixture of 4 fungi (*Geotrichum candidum, Penicillium crysogenum, Penicillium corylophilum, Fusarium* sp.) and 5 bacterial strains (*Pseudomonas aeruginosa, Pseudomonas fluorescens, Pseudomonas putida, Pseudomonas testosteroni, Bacillus fusiformis*). The inoculation is repeated 10 times with 3–4 days interval, and each time the paint is inoculated, the outgrowth of microorganims in the paint is evaluated by spreading of 10 μL paint on TSB-agar plates. Growth is measured as the number of out growing colonies and if more than 200 colonies are counted then the paint is considered putrefied.

| Sample | Laccase (mg/L) | Methylsyringate (μM) | Colony counts after 6 inoculations (CFU/ml paint) |
| --- | --- | --- | --- |
| 1 | 0 | 0 | $5.2 \times 10^3$ |
| 2 | 0 | 200 | $7.7 \times 10^3$ |

-continued

| Sample | Laccase (mg/L) | Methylsyringate (μM) | Colony counts after 6 inoculations (CFU/ml paint) |
|---|---|---|---|
| 3 | 0 | 400 | >2 × 10⁴ |
| 4 | 5 | 200 | 0 |
| 5 | 10 | 200 | 0 |
| 6 | 5 | 400 | 0 |
| 7 | 10 | 400 | 0 |

Growth was obtained in the paint after 6 inoculations. The laccase system results in a total inhibition of microbial outgrowth, whereas the methylsyringate showed no antimicrobial activity unless combined with the enzyme.

What is claimed is:

1. A paint composition comprising
   (a) a peroxidase or laccase;
   (b) an enhancer (i) of the following formula:

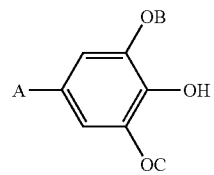

wherein A is —D, —CH=CH—D, —CH=CH—CH=CH—D, —CH=N—D, —N=N—D, or —N=CH—D, in which D is selected from the group consisting of —CO—E, —SO$_2$—E, —N—XY, and N$^+$—XYZ, in which E is —H, —OH, —R, or —OR, and X, Y and Z are identical or different and are —H or —R; wherein R is a C1–C16-alkyl group, which is saturated or unsaturated, branched or unbranched, and unsubstituted or substituted with a carboxy, sulpho or amino group; and B and C are identical or different and are $C_mH_{2m+1}$, wherein m is 1, 2, 3, 4 or 5; or (ii) is an inorganice halide ion;
   (c) an oxidizing agnet;
   (d) a viscosifier selected from the group consisting of polyarcylates, polyurethane and cellulose derivatives;
   (e) an acrylic compound;
   (f) at least 10% w/w water;
   (g) a pigment; and
   (h) a solvent.

2. The composition of claim 1, wherein the composition comprises a laccase.

3. The composition of claim 2, wherein the laccase is obtained from a strain selected from the group consisting of *Coprinus, Myceliophthora, Polyprous, Rhizoctonia*, and *Schytalidium*.

4. The composition of claim 1, wherein the composition comprises a peroxidase.

5. The composition of claim 4, wherein the peroxidase is obtained from a strain of *Coprinus*.

6. The composition of claim 4, wherein the peroxidase is a haloperoxidase.

7. The composition of claim 6, wherein the haloperoxidase is obtained from a strain selected from the group consisting of *Altemaria, Curvuaira, Dendryphiella, Drechsiera, Geniculosporium*, and *Phaeotrichoconis*.

8. The composition of claim 7, wherein the haloperoxidase is obtained from *Curvularia inaequalis* CBS, *Curvularia verruculosa Curvulaeria verruculosa, Dendryphiella saline, Drechsiera hartlebii, Geniculosporium* sp. or *Phaeotrichonconis crotalarie*.

9. The composition of claim 1, comprising two or more enhancers.

10. The composition of claim 1, wherein the enhancer is an enhancer of the following formula:

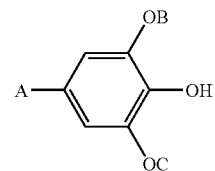

wherein A is —D, —CH=CH—D, —CH=CH—CH=CH—D, —CH=N—D, —N=N—D, or —N=CH—D, in which D is selected from the group consisting of —CO—E, —SO$_2$—E, —N—XY, and N$^+$—XYZ, in which E is —H, —OH, —R, or —OR, and X, Y and Z are identical or different and are —H or —R; wherein R is a C1–C16-alkyl group, which is saturated or unsaturated, branched or unbranched, and unsubstituted or substituted with a carboxy, sulpho or amino group; and B and C are identical or different and are $C_mH_{2m+1}$, wherein m is 1, 2, 3, 4 or 5.

11. The composition of claim 10, wherein the enhancer is methyl syringate.

12. The composition of claim 1, wherein the oxidoreductase is a haloperoxidase and the enhancer is an inorganic halide ion.

13. The composition of claim 12, wherein the inorganic halide ion is 0.05–500 mM chloride ions and 0.01–100 mM bromide or iodide ions.

14. The composition of claim 1, comprising between about 0.01 to about 1000 mg enzyme protein per liter composition.

15. The composition of claim 1, comprising 10–90% w/w water.

16. The composition of claim 1, comprising 5–50% w/w of a binder.

17. The composition of claim 1, comprising 0.001–500 mM of the oxidizing agent.

18. The composition of claim 1, further comprising one or more of filters, dispersants, foam suppressors and siccatives.

* * * * *